United States Patent [19]

Gerber

[11] Patent Number: 5,315,115
[45] Date of Patent: May 24, 1994

[54] OPTICAL APPARATUS AND METHOD FOR SENSING PARTICULATES

[76] Inventor: Hermann E. Gerber, 1643 Bentana Way, Reston, Va. 22090

[21] Appl. No.: 926,695

[22] Filed: Aug. 10, 1992

[51] Int. Cl.$^5$ .............................. G01N 21/49
[52] U.S. Cl. .................. 250/338.1; 250/340; 356/336
[58] Field of Search ............... 250/338.1, 340; 356/336, 335, 338; 359/558

[56] References Cited

U.S. PATENT DOCUMENTS 3,705,771  12/1972  Friedman et al.
3,873,206   3/1975  Wilcock
4,037,964   7/1977  Wertheimer et al.
4,363,551  12/1982  Achter et al.
4,597,666   7/1986  Gerber et al.

OTHER PUBLICATIONS

Wertheimer et al., "Light Scattering Measurements of Particle Distributions", Applied Optics, vol. 15, No. 6:1616–1620 (U.S.A. Jun. 1976).
Blyth et al., "An Optical Device for the Measurement of Liquid Water Content in Clouds", Quart. J. R. Met. Soc., 110:53–63 (Great Britain, 1984).

Primary Examiner—Paul M. Dzierzynski
Assistant Examiner—Richard Hanig
Attorney, Agent, or Firm—James Creighton Wray

[57] ABSTRACT

The present invention relates to an apparatus and method of determining particulate integrated properties consisting of integrated volume concentration, integrated surface area concentration and aerosol extinction coefficient in the infrared portion of the light spectrum using a noncollimated light beam irradiating suspended particulates. A light trap is placed in front of the lens that collects the light scattered by the particulates. Two separate detectors are placed differently with respect to the noncollimated beam to measure the light scattered by the particulates. Variable transmission filters are placed in front of the detectors to correct for the distortions in the light scattered by the particulates due to the off-axis intensity of the noncollimated beam.

7 Claims, 3 Drawing Sheets

OPTICAL APPARATUS AND METHOD FOR SENSING PARTICULATES

BACKGROUND OF THE INVENTION

This invention relates to optically measuring the following properties of suspended polydisperse particulates: integrated volume concentration, integrated surface area concentration, and aerosol infrared extinction coefficient. These properties can be given the name particulate integrated properties.

Other optical techniques exist to measure the preceding integrated properties of particulates. These techniques can be categorized into two broad types: In the first type, a light beam is used to irradiate one particulate at a time, and the light scattered out of the beam by the particulate and measured by a light detector gives an indication of the desired property of the particulate. A typical example of this single-particulate optical technique is described by W. D. Bachalo, U.S. Pat. No. 4,854,705, Aug. 8, 1989. In order to determine the volume, area, and extinction particulate integrated properties listed in the preceding, such single-particulate optical techniques are required to sum up electronically the light-scattering contribution from many individual particulates.

Given the small size of typical particulates, which is often in the order of microns, and the resulting requirement for microminiature and highly precise measuring optics, it is difficult for the single-particulate optical techniques to achieve high accuracy in the measurement of the particulate integrated properties. The second broad type for optically measuring particulates minimizes this difficulty, because in the second type a light beam irradiates many particulates in the same time interval, and the light scattered by the many particulates is measured by a detector that can output a signal directly proportional to the particulate integrated properties. Examples of this multiple-particulate optical technique are given by W. L. Wilcock, U.S. Pat. No. 3,873,206, Mar. 25, 1975, and H. E. Gerber, U.S. Pat. No. 4,597,666, Jul. 1, 1986.

The previous multiple-particulate optical techniques use a collimated light beam to irradiate the particulates. The collimated-beam feature permits the use of simple detector geometries (for example, slit-like for the Wilcock patent, and circular detector for the Gerber patent) to determine directly particulate integrated properties; however, the collimated-beam feature leads to some limitations that the present invention attempts to overcome. In the earlier techniques the collimated beam and scattered light usually pass through a lens, on the other side of this lens the beam is focused into a light trap, and the scattered light continues on to a large-area detector placed just past the light trap. The beam passing through this lens scatters light from unavoidable imperfections in the glass of the lens, as well from possible contamination on the lens, surfaces; this scattered light interferes with the measurement of light scattered by the particulates, and prevents the use of this technique (with collimated beam passing through lens) for measuring particulate concentrations and mass loadings important for environmental monitoring. An obvious alternative is to place the light trap in front of the lens, so that the collimated beam is not required to pass through the lens. This alternative, however, requires that the collimated beam and light trap are very narrow, so that the required small light-scattering angles from the particulates are not blocked from the detector. The narrow beam of this alternative results in a small irradiated volume that under conditions of low particulate concentration is a disadvantage.

This patent application described an optical method and apparatus that utilizes a noncollimated convergent beam irradiating many particulates in the same time interval. The convergent beam falls into a light trap in front of the lens that collects the scattered light. In this manner no light from the beam is scattered by the lens; and the noncollimated beam can illuminate a much larger volume containing particulates than can the narrow collimated beam. This leads to an apparatus that is more sensitive to low particulate concentrations, and that can be more compactly constructed.

The use of a convergent noncollimated beam does not, however, lend itself to the simple and direct measurement of the particulate integrated properties obtained with the simple detector geometries used in the collimated-beam techniques. This invention describes a method, based on using an inversion spatial filter placed in front of the detector, by which the present noncollimated technique can make direct measurements of particulate integrated properties.

This invention further describes the use of a second detector assembly placed in such a way with respect to the concollimated beam to enhance the scattered light contribution from small particulates, which are underestimated in the single detector version. This permits a particulate size range to be measured (0.1 um and larger) for the particulate integrated properties that is consistent which required atmospheric monitoring.

SUMMARY OF THE INVENTION

It is therefore an object of the invention to provide a method to measure particulate integrated properties consisting of integrated volume concentration, integrated surface area concentration, and aerosol extinction coefficient in the infrared portion of the light spectrum with an apparatus that utilizes a noncollimated light beam irradiating suspended particulates.

It is further an object of this invention to provide an apparatus with sufficient sensitivity and accuracy to permit measuring particulate volume concentrations (also termed mass loading, if particulate density is known) as small as several microgram per meter cubed, which is consistent with environmental monitoring requirements.

It is further an object of this invention to provide an apparatus for measuring particulate integrated properties for a particulate size range extending to particulates as small as 0.1 um which is also a requirement for ambient monitoring.

The preceding objectives are realized in the method and apparatus of this invention by utilizing a convergent noncollimated light beam irradiating suspended particulates, placing a light trap for the beam in front of the lens that collects the light scattered by the particulates, utilizing two separate detectors placed differently with respect to the noncollimated beam to measure light scattered by the particulates, and utilizing variable transmission filters in front of the detectors to correct for the distortions in the particulates, scattered light field due to the off-axis intensity of the noncollimated beam.

DESCRIPTION OF PREFERRED EMBODIMENTS

Figure 1:
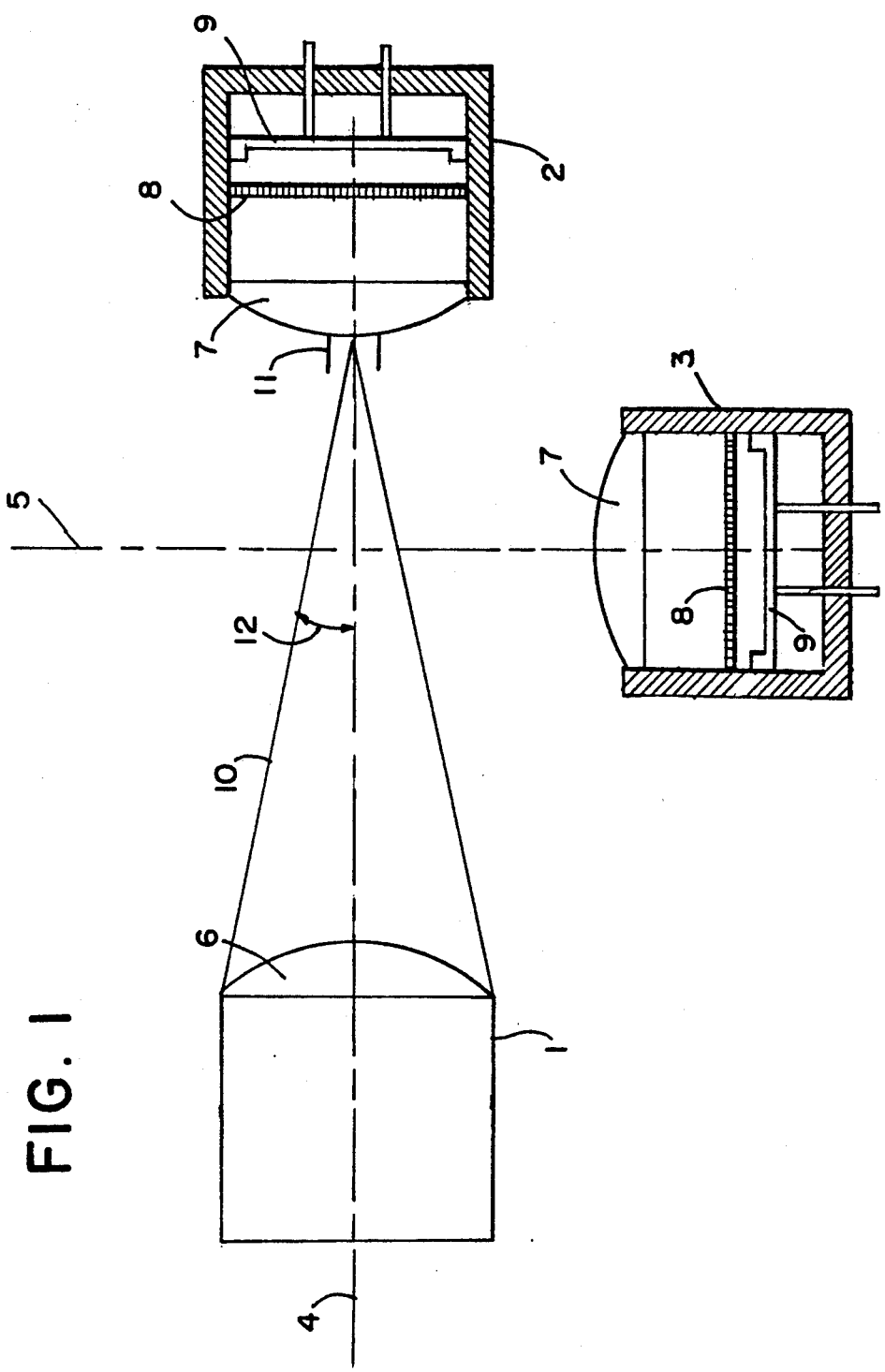
FIG. 1—Preferred embodiment of the present invention.

The visible or near-infrared light source 1 shown in the preferred embodiment sketched in FIG. 1 generates a convergent light beam 10 that falls within light trap 11. The half angle of convergence 12 of the light beam is typically 2.5 deg. to 5 deg. Particulates are irradiated by the light beam 10 when they are found in or pass through the beam 10. Given that the volume of 10 is large in comparison to the typical volume occupied by individual particulates, many particulates will be found at any given time within the volume defined by the light beam 10. If the concentration of particulates is very low so that only a few particulates are in volume 10 at any given time, then the measurement of the desired particulate integrated property requires an average measurement over a sufficiently long time interval to expose a larger number of particulates to the irradiation from the beam.

The light scattered by the particulates located in the beam 10 is scattered into the detector lenses 7 of the detector assembly 2 placed coaxial with the optical axis 4 of the light source 1, and of the detector assembly 3 placed with the optical axis 5 perpendicular to optical axis 4. The location of optical axis 5 is the preferred embodiment; other embodiments are feasible with axis 5 placed at different angles with respect to axis 4 in order to enhance or decrease the particulate scattering contribution from the small size fraction of particulates.

The light scattered by the particulates passing through the detector lenses 7 falls on a spatial filter 8 located at the focal plane of each detector lens 7. The spatial filters consist of concentric filter elements 16 (see FIG. 2 and FIG. 3), with the radius R of each element measured from the optical axes 4, 5 to the element. Each circular concentric filter element transmits a fraction of the scattered light impinging on it; this transmission T as a function of R is given the functional definition of T(R). After passing through the spatial filters 8 the scattered light impinges on light detectors 9 that have a sensitive area as large or larger than the spatial filters 8.

Figure 2:
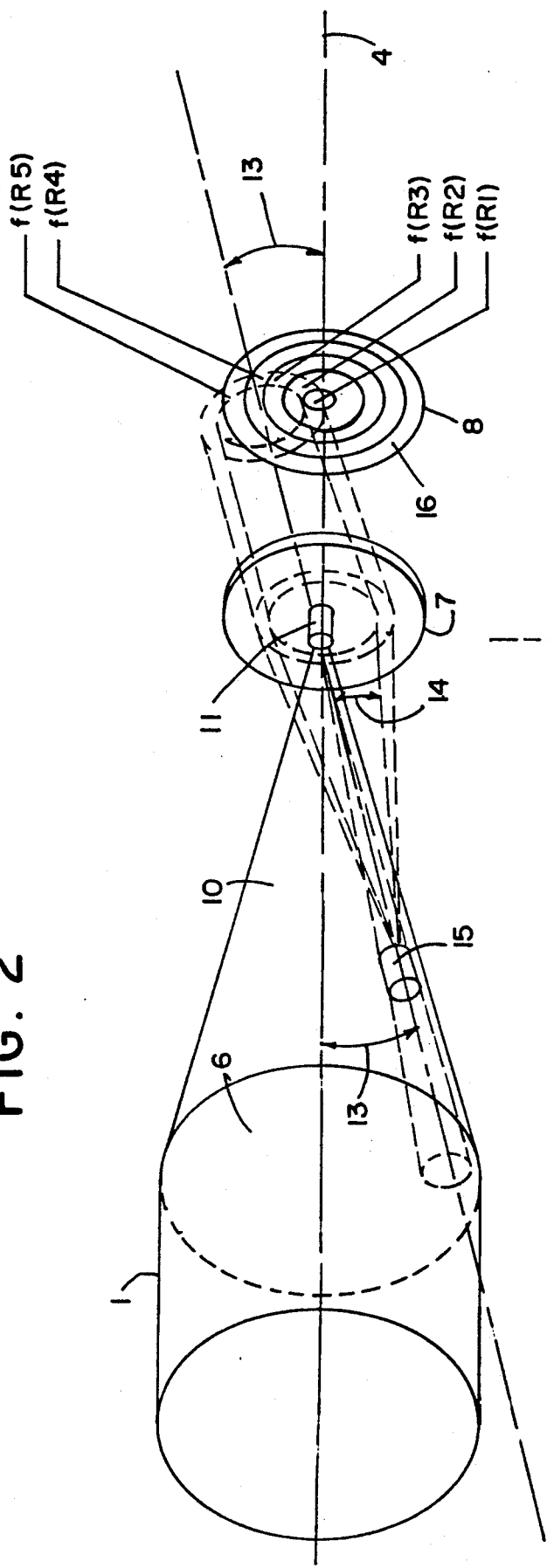
FIG. 2—Oblique view of light source, detector lens, and spatial filter of present invention, illustrating off-axis scattered particulate light pattern from one off-axis intensity element of the convergent light beam.
Figure 3:
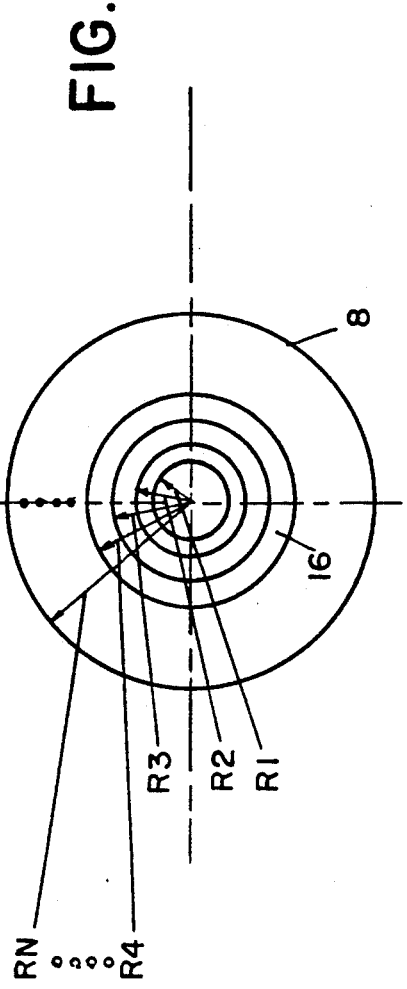
FIG. 3—Spatial filter placed in front of the detectors, with R1, R2 ... RN the radii of concentric filter elements each with its own light transmission T(R) value.

As a consequence of the convergent light beam light scattered by particles irradiated by light-intensity elements off the optical axis 4 form a scattering pattern that is non-symmetrical with respect to the concentric filter elements 16 of the spatial filter 8. This consequence is illustrated in FIG. 2, where intensity element d1 15 scatters light from particulates at an angle 14. While the diagram in FIG. 2 only shows parts of detector assembly 2, a similar diagram holds for detector assembly 3 which is not shown. As shown in FIG. 2 this scattered light impinges on the spatial filter 8 nonsymmetrically; that is, the scattering pattern is not coaxial with the optical axis 4. (In the case of a collimated beam used in previous instrumentation, the scattering pattern would be coaxial with the axis 4, which results in direct measurements of integrated particulate properties.) The flux of scattered light impinging on each concentric filter element 16 for the present nonsymmetrical case is illustrated in FIG. 2, and is given by f(R1), f(R2) ... for the present nonsymmetrical convergent-beam configuration, from the symmetrical coaxial case that requires no correction, the transmission of each concentric filter element 16 is specified by the following method:

The total scattered light flux seen by detectors 9 given by $$F = F1 + F2$$

where, for example the total scattered light flux seen by the detector 9 in detector assembly 2 is given by $$F1 = \sum_I \sum_R f(Rn) \, T(R) \, \Delta R \, \Delta I \tag{2}$$

where a similar expression holds for F2. f(Rn) is a function of the distance of the scattering intensity element 15 from the detector lens 7, of the light scattering angle 14, and of the diameter of the scattering particles.

Equation (2) is an integral that has the transmission T(R) of the concentric filter elements 16 under the double summation (integral) sign. It is necessary to mathematically invert this double integral to discover whether a set of T(R) values exists that correct for the distortion caused in the scattered light by the nonsymmetrical scattered-light geometry caused by the convergent light beam. To illustrate this need f(Rn) in Eq. (2) is evaluated as a function of particulate size for concentric filter elements 16 for different element radii R, under the condition that all $T(R)=1$, which is equivalent to eliminating the spatial filters 8 from the apparatus. Given that the detector (sensor) output is normalized by the particulate size cubed, the curves in FIG. 4 should generate a horizontal straight line over the particulate size range of interest, for the case where the apparatus should measure integrated particulate volume. Clearly, the sum of the curves in FIG. 4 will not be the required straight line; this sum will have a shape similar to the bell-shaped curve labeled "with/out inversion" in FIG. 6.

Figure 4:
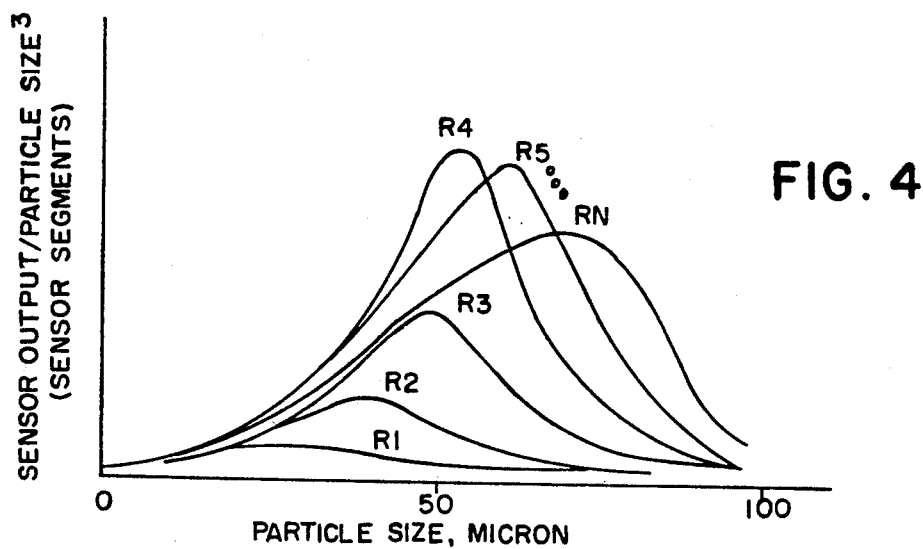
FIG. 4—Detectors' (sensor) output normalized by the diameter cubed of the particulates as a function of particulate diameter, and for concentric filter elements for different values of element radius R and for all $T(R)=1$.
Figure 5:
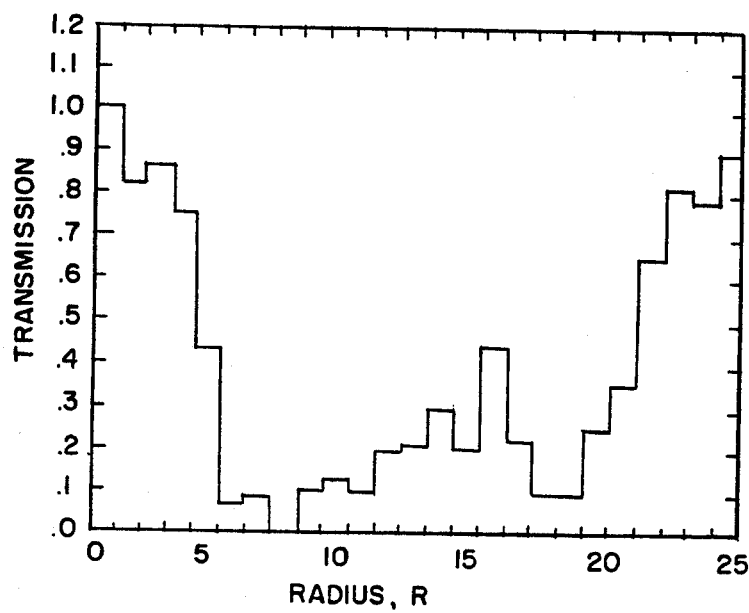
FIG. 5—Transmission of concentric filter elements as a function of element radius R determined by inverting the mathematical integral for total scattered light flux measured by the detectors to achieve an output of the apparatus proportional to the integrated particulate volumn concentration.
Figure 6:
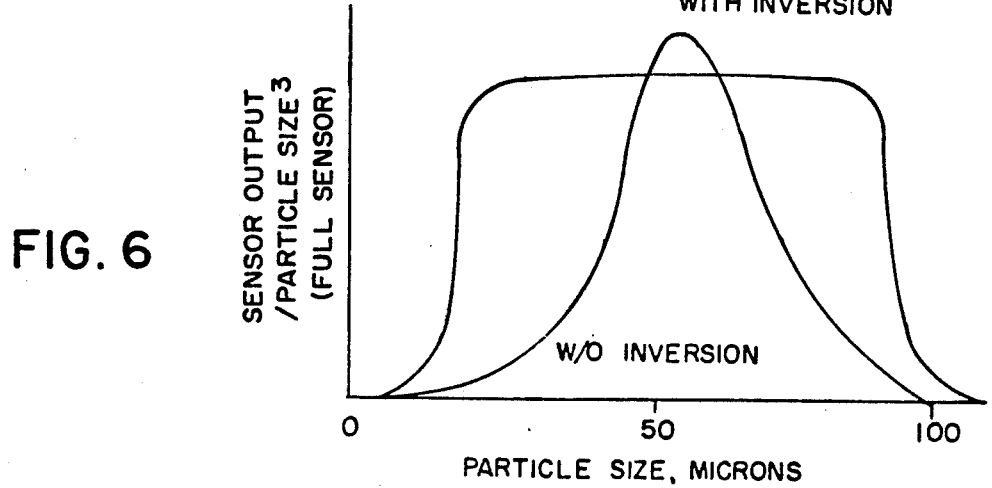
FIG. 6—Total flux of the detectors as a function of particulate diameter for $T(R)=1$, and for inversion values of T(R) shown in FIG. 5.

When Eq. (2) is inverted mathematically to determine if a pattern of T(R) can be found that will correct for the scattered-light distortions caused by the present configuration, a pattern of T(R) results as shown in FIG. 5. This pattern of T(R) gives the needed spatial filter 8 transmission values for spatial filters 8 that consist of 25 different concentric filter elements 16. When the spatial filter 8 with the pattern in FIG. 4 is used in the present apparatus a direct measure of the particulate volume concentration is possible. The effect of this filter 8 on the output of the apparatus is shown in FIG. 6, where the required horizontal straight line "with inversion" results when the filter with the transmission function T(R) shown in FIG. 5 is used.

It has also been discovered that inversions of Eq. (2) will yield other spatial filter 8 transmission functions T(R) that cause the apparatus to directly output other particulate integrated properties, including the integrated surface concentration, and the aerosol extinction coefficient in the infrared.

It should be realized by experts in the field of light scattering by particulates that there are embodiments of the present invention other than the preferred embodiment described here. It is likely that other integrated particulate properties can be determined with the method described in this invention. Geometries similar to the present embodiment are also possible for obtaining similar integrated particulate properties; these include using the second detector assembly 3 with its optical axis 5 at an angle different from the one illustrated here, using more than two detector assemblies, using different light beam geometry, and using other than a visible or near-infrared light source.

I claim:

1. A method for measuring integrated properties of suspended particulates consisting of the following steps:
   Irradiating particulates suspended in a noncollimated light beam with the light beam, measuring with a detector the light scattered by the particulates over a time interval sufficiently long that many particles contribute to the scattered light, correcting the distortion of the scattered light due to off-axis light intensity of the noncollimated beam by placing an inversion spatial filter in front of the scattered-light detector and at the focal point of the detector lens used for collecting light scattered from the particulates.

2. The method of claim 1 where the particulate integrated properties are the integrated particulate volume concentration, the integrated particulate surface area concentration, and the aerosol extinction coefficient in an infrared portion of the light spectrum; all three properties measured over a particular particulate size range.

3. The method of claim 1 where the noncollimated light beam is a convergent beam.

4. The method of claim 1 where the spatial filter has concentric variable light transmission elements each of which has the light transmission through it, necessary for correcting the distortion in the scattered light caused by the off axis light beam intensity, determined by inverting the total particulate scattered-light flux integral.

5. Apparatus for measuring integrated properties of suspended particulates consisting of the following parts:
   Light source coaxial with converging light beam falling into a light trap placed in front of the detector lens for collecting light scattered by the particulates, with inversion spatial filter located at the focal point of the detector lens, and with detector placed adjacent to the inversion spatial filter, the light trap, detector lens, spatial filter, and detector forming the first detector assembly wherein the particulates located in and irradiated by the convergent light beam scatter light into the first detector assembly, where the inversion filter corrects the distortion in the scattered light due to the off-axis light beam intensity, to yield directly particulate integrated properties as the detector output.

6. The apparatus of claim 5 wherein in the inversion filter corrects distortion to yield directly properties which comprise the integrated particulate volume concentration, integrated particulate surface area concentration, and aerosol extinction coefficient in the infrared part of the optical spectrum.

7. The apparatus of claim 5 where a second detector assembly consisting of detector lens, spatial filter at the focal length of the detector lens, and detector adjacent to the spatial filter is used simultaneously with the first detector assembly to enhance small particulate response, the second assembly is placed between the light source and the first detector assembly, outside of the convergent light beam, and with optical axis at an angle with respect to the optical axis of the alight source and first detector assembly.

* * * * *